United States Patent
Anapliotis

[19]

[11] Patent Number: 6,123,676
[45] Date of Patent: Sep. 26, 2000

[54] METHOD AND APPARATUS FOR DETECTING AN INCREASED RISK OF A PREMATURE BIRTH

[75] Inventor: Emmanuel Anapliotis, Berlin, Germany

[73] Assignee: Selfcare International, Oberhaging, Germany

[21] Appl. No.: 08/864,584

[22] Filed: May 28, 1997

[30] Foreign Application Priority Data

May 30, 1996 [DE] Germany .................. 296 10 236 U
Aug. 9, 1996 [DE] Germany .................. 296 14 429 U

[51] Int. Cl.[7] .................................................. A61B 10/00
[52] U.S. Cl. ...................... 600/551; 600/771; 600/588
[58] Field of Search ................................. 600/530, 584, 600/575, 572, 591, 588, 551; 2/161, 159, 163

[56] References Cited

U.S. PATENT DOCUMENTS 3,672,351  6/1972  Ubersax et al. .................... 600/572
4,078,656  3/1978  Crane et al. ........................ 600/572
4,245,656  1/1981  Farr et al. .......................... 600/591
4,367,750  1/1983  Levine ............................... 600/371
4,784,158  11/1988  Okimoto ............................ 600/584
5,063,930  11/1991  Nucci ................................. 600/366
5,609,160  3/1997  Bahl et al. .......................... 600/584
5,641,496  6/1997  Van Roekel ........................ 424/404

*Primary Examiner*—Cary O'Connor
*Assistant Examiner*—Pamela Wingood
*Attorney, Agent, or Firm*—Harness, Dickey & Pierce, P.L.C.

[57] ABSTRACT

An apparatus for use in measuring the properties of endogenous fluids during a medical examination. The apparatus includes a protective clothing article which is able to be used during the medical examination, as well as a diagnostic strip which is able to measure the pH of the endogenous fluid during the examination. In addition, the apparatus also includes a two-sided adhesive strip which is able to secure the diagnostic strip to a portion of the protective clothing article.

30 Claims, 8 Drawing Sheets

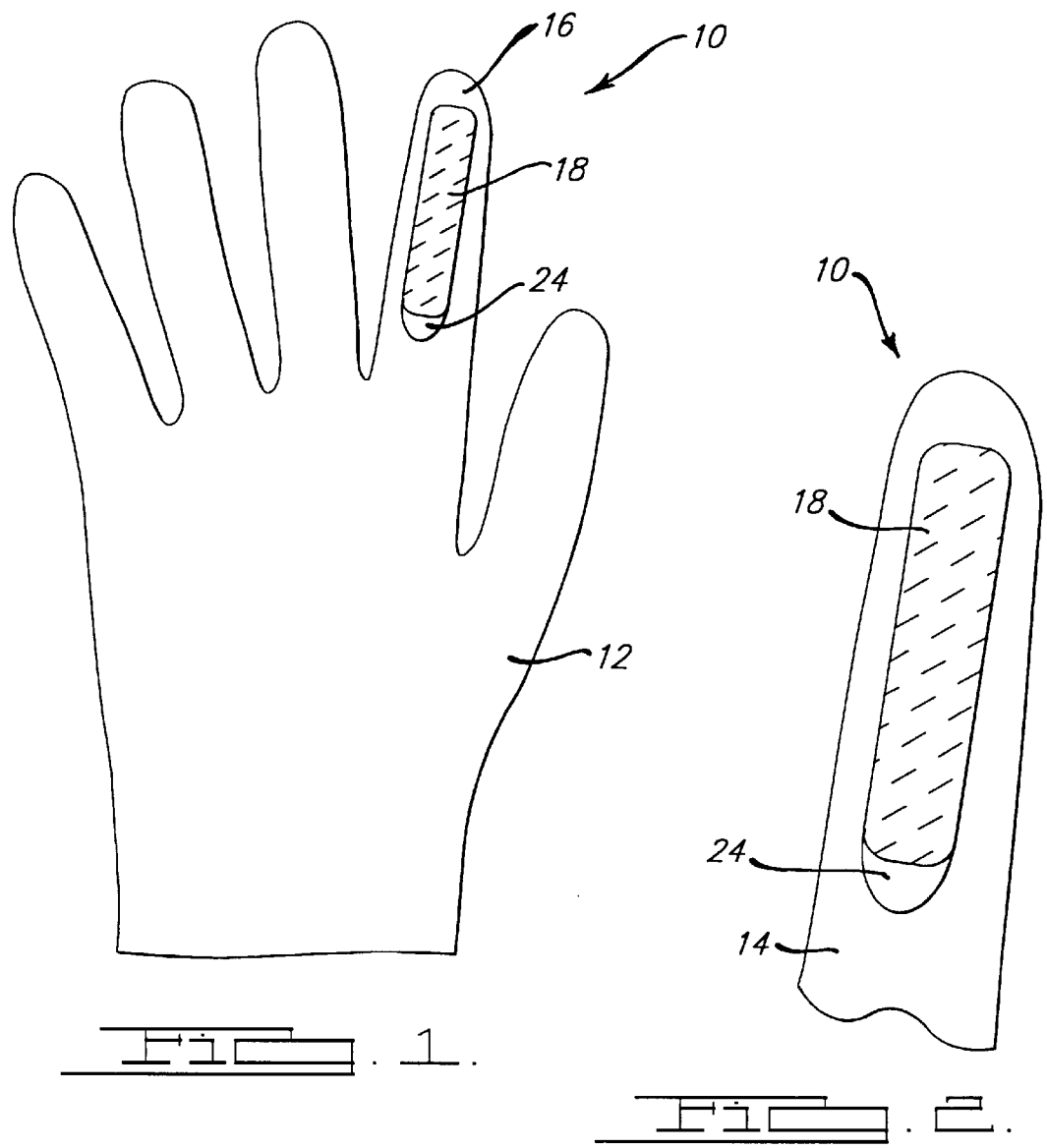
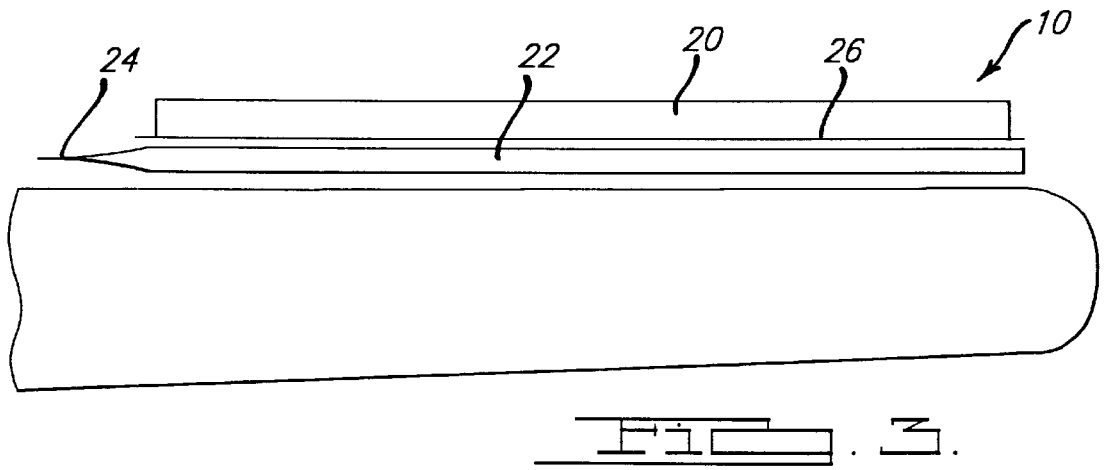

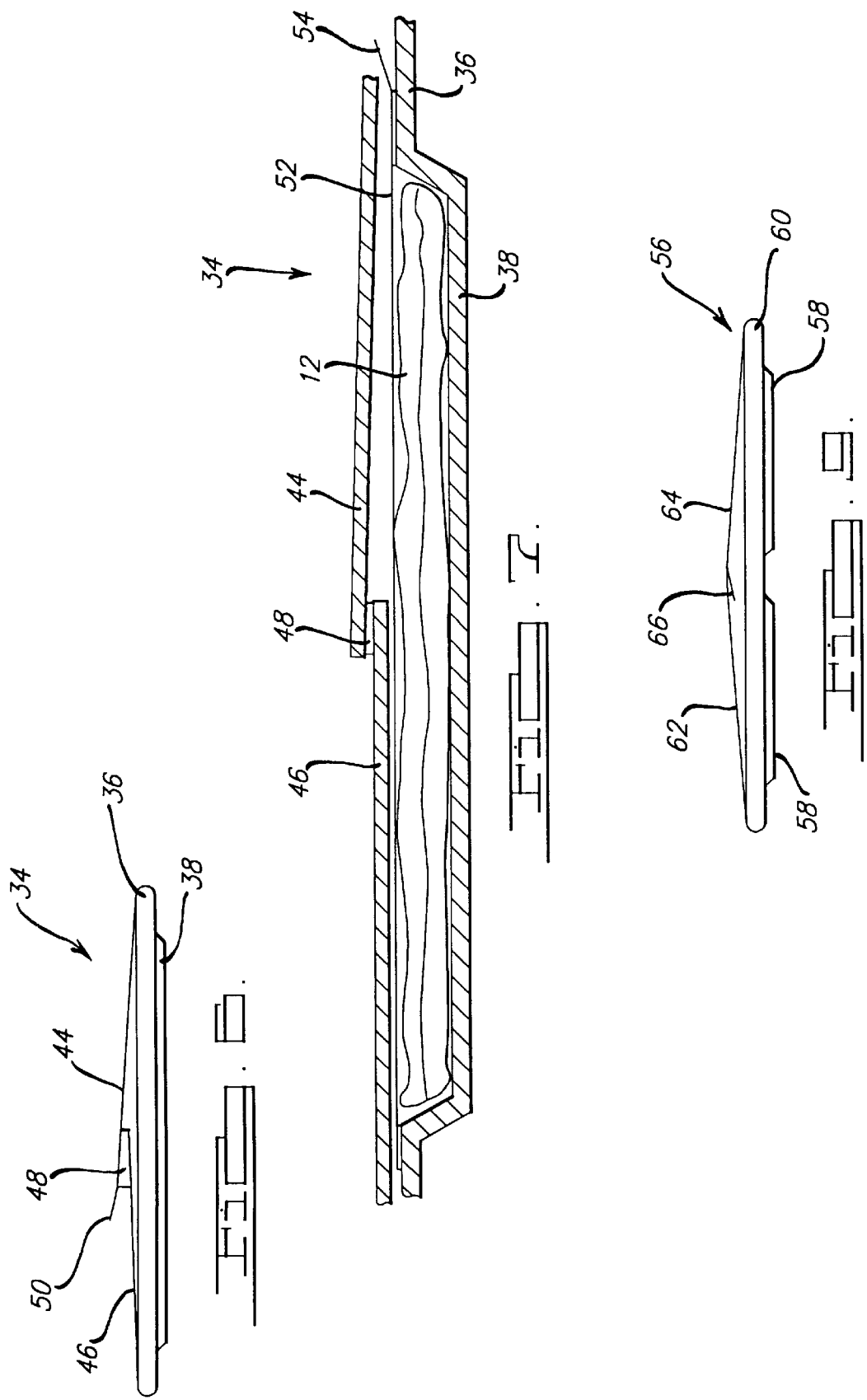

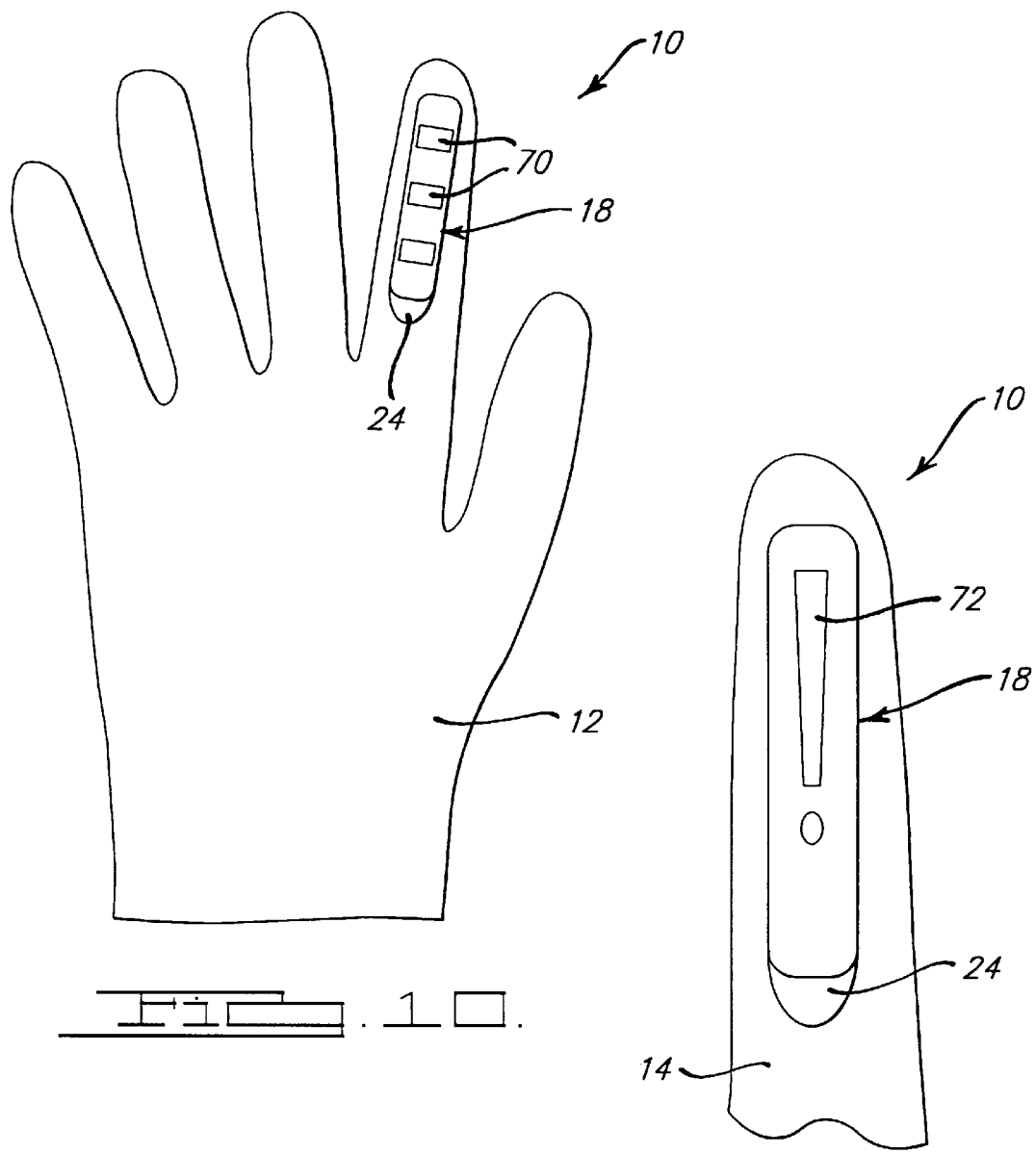

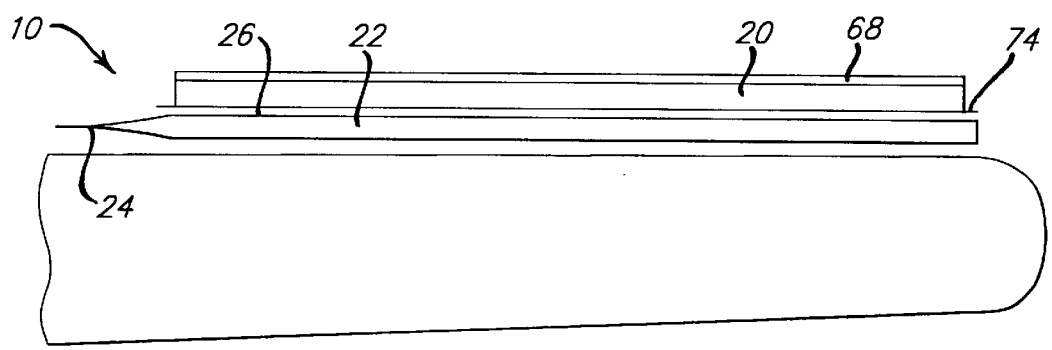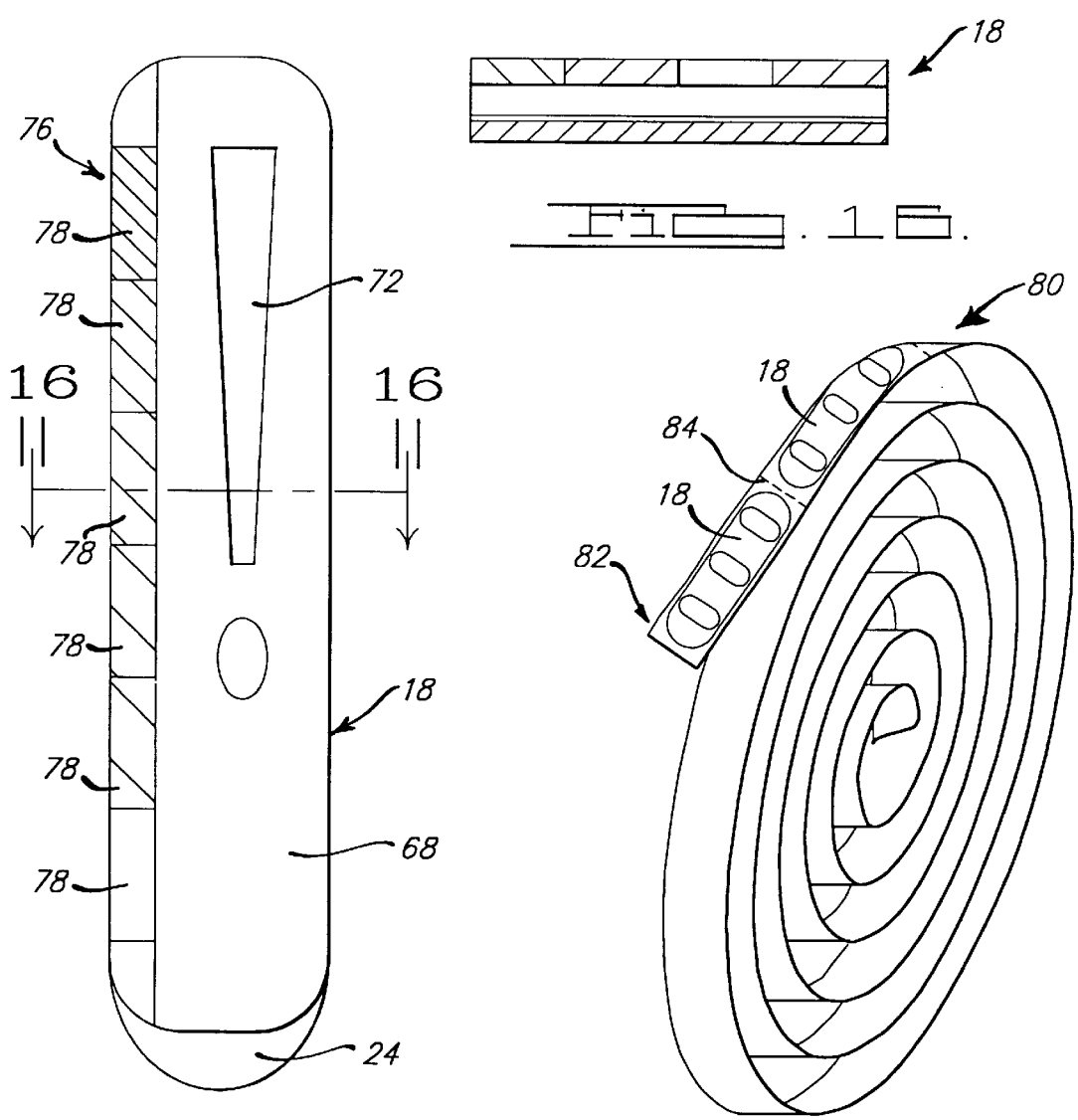

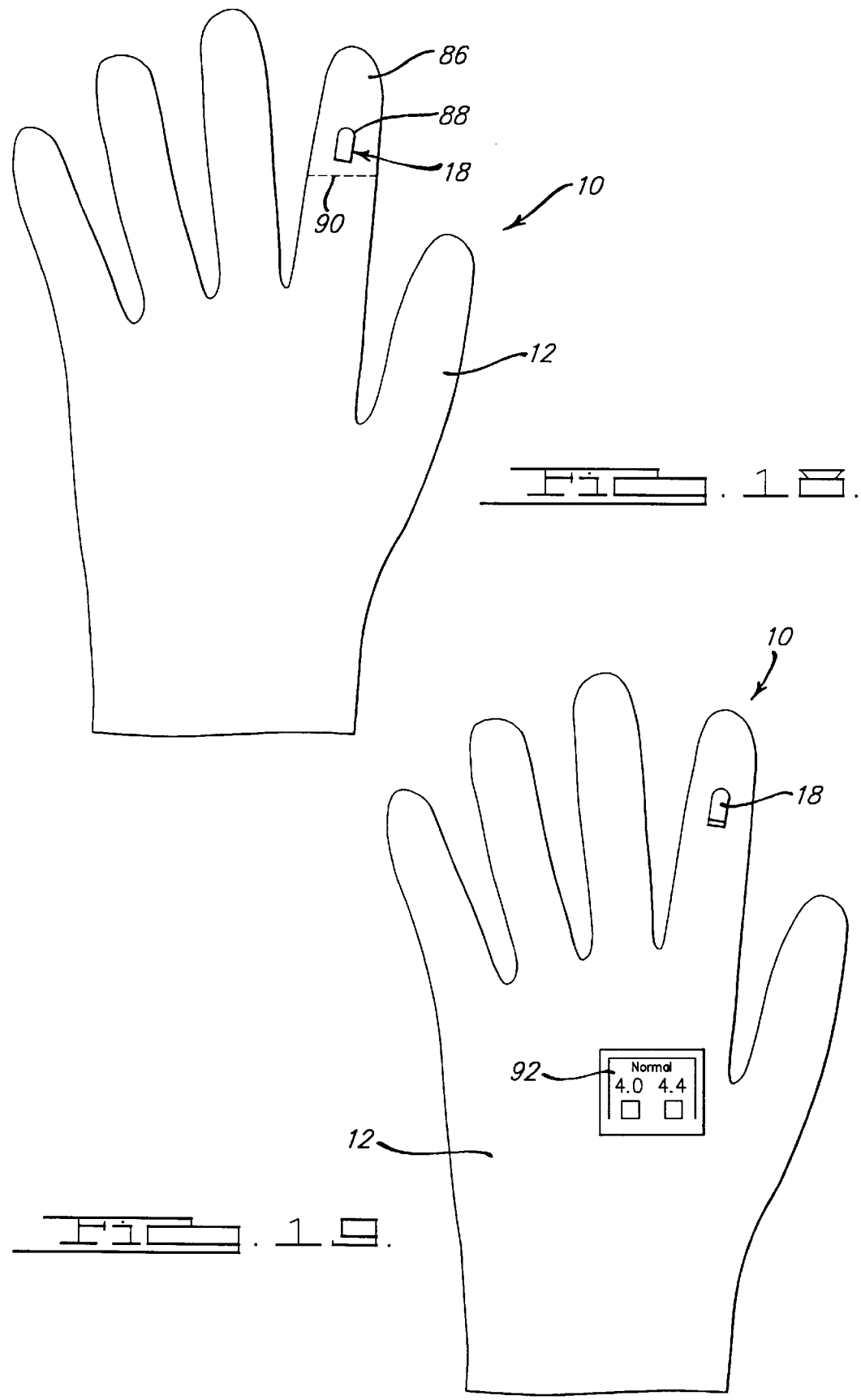

METHOD AND APPARATUS FOR DETECTING AN INCREASED RISK OF A PREMATURE BIRTH

BACKGROUND OF THE INVENTION

1. Field of the Invention

This invention relates to medical detection systems, and more particularly to a method and apparatus for determining whether a pregnant woman is at an increased risk of premature birth.

2. Description of the Related Art

One of the most common causes of premature birth is the colonization of infection causing bacteria in the vagina which, unfortunately, may go unnoticed by the expectant mother. Infection-causing bacteria inhibit the development of vaginal lactic acid-forming bacteria which normally creates an acidic environment that protects the vagina against foreign bacteria. The infection may spread to the uterus where it can lead to complications ranging from premature contractions to premature rupture and, ultimately, premature delivery. The more rapidly the infection is diagnosed, the better the chances of successful treatment and prevention of premature birth.

More than fifty percent of all women of childbearing age suffer from vaginal infections. In addition, women at an age of 30 to 39 are also often affected by recurrent infections. These infections are often the result of an imbalance in the vaginal environment.

It has recently been determined that disturbance of the natural balance of the vaginal-flora may lead to a change in the acidity of the vaginal fluid and therefore to an increase in the pH of vaginal fluid. That is, pH indicates the acid content of the test substance which, in this case, is the vaginal fluid. Accordingly, the more acidic the vaginal fluid, the lower the pH.

German Utility Model DE-GM 94 07 486 discloses a examination glove for simultaneously measuring the pH of the vaginal fluid. This reference discloses an examination glove in which the examination finger of the glove has a diagnostic strip firmly attached which is able to determine the pH of the vaginal fluid. However, there are certain disadvantages associated with an examination glove of this form because there may be erroneous results when analyzed by the patient, as well as difficulties in qualitatively analyzing the diagnostic strip. In addition, it is difficult to affix the diagnostic strip reliably and relatively inexpensive in the form of a ready-made item.

SUMMARY OF THE INVENTION

The apparatus according to the preferred embodiment of the invention includes slip-on, elastic protective clothing article for measuring the pH of vaginal fluid during gynecological examinations. The protective clothing article has a diagnostic strip to be used for pH measurement which includes a two-sided adhesive strip which is able to secure the diagnostic strip to the protective clothing article. The use of a two-sided adhesive strip has the advantage that, on the one hand, the direct application of an adhesive to the protective clothing article is avoided and, on the other hand, the quantity of adhesive and the position of the adhesive are predetermined. Accordingly, contamination of the area of the protective clothing article where the diagnostic strip is to be secured, and in particular on the examination finger, by excess adhesive is also avoided. Such contamination may make the protective clothing article useless for the intended examination.

In accordance with an advantageous refinement of the invention, the adhesive strip includes a section shaped as a grip which is adhesive-free on both sides. This grip section facilitates handling of the diagnostic strip while placing the diagnostic strip on the protective clothing article. Equally favorable is the fact that the indicator layer of the diagnostic strip does not have to be touched while positioning the diagnostic strip on the protective clothing article. In this way, contamination of the indicator layer is avoided which may lead to a falsification of the pH measurement and would make another examination necessary.

According to another preferred embodiment of the present invention, the elastic protective clothing article includes a diagnostic strip which has an indicator layer and a covering layer. The covering layer partially covers the indicator layer of the diagnostic strip so that only a portion of the indicator layer reacts to pathological change of the endogenous fluids. Accordingly, a change in color of portions of the indicator layer can easily be detected by comparing the covered portions of the indicator layer with the uncovered portions of the indicator layer.

According to another embodiment of the invention, the covering layer of the diagnostic strip is formed from a monochrome opaque film in which circular or square cutouts are provided. These cutouts expose sections of the surface of the indicator layer to endogenous fluid. The monochrome opaque film is fastened to the indicator layer by adhesion.

According to another embodiment of the invention, the covering layer has a coloration which substantially matches the hue that the indicator layer assumes when the vaginal fluid has the pH value corresponding to the healthy vaginal milieu. This causes the coloration of the diagnostic strip to be substantially uniform over its entire surface if the vaginal milieu does not exhibit any pathological changes. In case of a pathological vaginal milieu, only the sections of the indicator layer exposed to the vaginal fluids through the cutouts change color so that the color change is easily perceptible by comparing the discolored area of the indicator layer with the region of the covering layer adjacent to it.

According to another embodiment of the invention, the cutouts provided in the covering layer can take the shape of a particular symbol or phrase. For example, the cutouts could be shaped as a warning or caution symbol, or character such as an exclamation point. By shaping the cutouts of the covering layer in this manner, two visual indications would be present when there is a change of the endogenous fluid: (1) a change in color of portions of the indicator layer not covered by the covering layer and (2) the appearance of the symbol.

According to yet another embodiment of the invention, a number of identically constructed diagnostic strips are detachably mounted in a sequential arrangement on a support strip. The support strip is wound up into a tear-off roll and has a planned tearing point between each two successive diagnostic strips. This form of storage of the diagnostic strips permits easier handling of the diagnostic strips when the protective clothing articles used for the medical examination are to be equipped as needed with a diagnostic strip.

BRIEF DESCRIPTION OF THE DRAWINGS

Various advantages of the present invention will become apparent to one skilled in the art upon reading the following specification and by reference to the following drawings in which:

FIG. 1 is a elevational view of the apparatus for detecting an increased risk of premature birth in the form of a glove according to one preferred embodiment of the present invention;

FIG. 2 is an elevational view of the apparatus for detecting an increased risk of premature birth according to another preferred embodiment of the present invention in which the protective clothing article takes the form of a finger stall;

FIG. 3 is a side elevational view of the protective clothing article showing FIGS. 1 and 2 showing the diagnostic strip according to one preferred embodiment of the present invention;

FIG. 6 is a side elevational view of the packaging used in connection with the apparatus for detecting an increased risk of premature birth shown in FIG. 5 according to one preferred embodiment of the present invention;

FIG. 7 is a cross sectional view of the packaging associated with the apparatus for detecting an increased risk of premature birth taken along the lines 7—7 in FIG. 5 according to one preferred embodiment of the present invention;

FIG. 9 is a side elevational view of the packaging associated with the apparatus for detecting an increased risk of premature birth shown in FIG. 8 according to one preferred embodiment of the present invention;

FIG. 10 is an elevational view of the apparatus for detecting an increased risk of premature birth according to another embodiment of the present invention in which the protective clothing article takes the form of a glove;

FIG. 11 is an elevational view of the apparatus for detecting an increased risk of premature birth according to another embodiment of the present invention in which the protective clothing article takes the form of a finger stall;

FIG. 12 is an elevational view of the covering layer associated with the diagnostic strip of the apparatus for detecting an increased risk of premature birth according to another embodiment of the present invention;

FIG. 13 is an elevational view of the covering layer associated with the diagnostic strip of the apparatus for detecting an increased risk of premature birth according to another preferred embodiment of the present invention;

FIG. 14 is a side elevational view of the apparatus for detecting an increased risk of premature birth shown in FIGS. 10 and 11 according to another embodiment of the present invention;

FIG. 15 is a top elevational view of the diagnostic strip used in conjunction with the apparatus for detecting an increased risk of premature birth according to another embodiment of the present invention;

FIG. 16 is a cross-sectional view of the apparatus for detecting an increased risk of premature birth according to another preferred embodiment of the present invention taken along the lines 16—16 in FIG. 15;

FIG. 17 is an illustration of a tear-off roll in which a plurality of diagnostic strips are located which are used with the apparatus for detecting an increased risk of premature birth according to another embodiment of the present invention;

FIG. 18 is an elevational view of the apparatus for detecting an increased risk of premature birth according to one embodiment of the present invention;

FIG. 19 is an elevational view of the apparatus for detecting an increased risk of premature birth according to yet another embodiment of the present invention.

DETAILED DESCRIPTION OF THE PREFERRED EMBODIMENT

Figure 4:
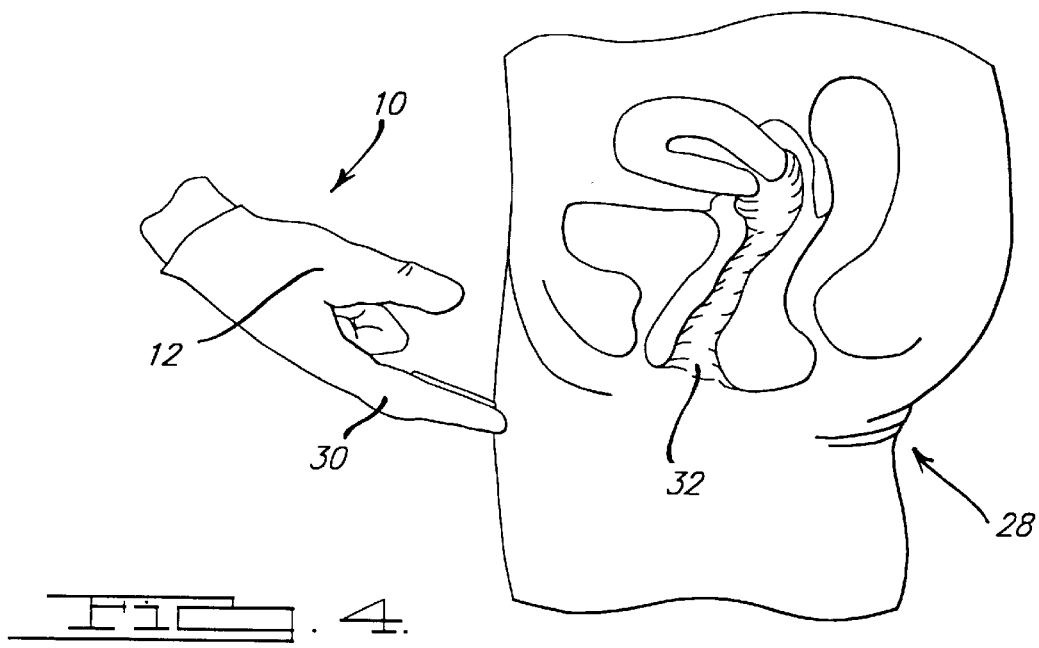
FIG. 4 illustrates the method for detecting an increased risk of premature birth according to one preferred embodiment of the present invention.

The following discussion of the preferred embodiment of the present invention is merely exemplary in nature and is not intended to limit the invention or its application or uses.

Referring now to FIGS. 1 and 2, there is shown an apparatus for detecting an increased risk of a premature birth according to one preferred embodiment of the present invention. The apparatus is shown in the form of a protective clothing article 10 which takes the form of a glove 12 as shown in FIG. 1 or a finger stall 14 as shown in FIG. 2. The glove 12 includes a finger section 16 which corresponds to the index finger (hereinafter referred to as the "examination finger") and is preferably used for the examination. However, the use of a finger stall 14 equipped with a diagnostic strip as described below permits the gynecologist or patient to select individually which finger is to be used for the examination and on which side of the finger the diagnostic strip is to be positioned. It will be appreciated that other suitable protective clothing articles 10 may be used.

The protective clothing article 10 is preferably made of polyethylene, since a particularly good adhesion is attainable with this material in a simple manner between the diagnostic strip and protective clothing article by means of a two-sided adhesive strip as will be discussed below. While the protective clothing article 10 may be used in determining the pH level of vaginal fluid, it is to be understood that the protective clothing article 10 may also be used with detecting characteristics of other forms of endogenous fluid as well.

The protective clothing article 10 includes a diagnostic strip 18. The diagnostic strip 18 is disposed on the protective clothing article 10 in the region of the protective clothing article 10 which is used during the examination. The diagnostic strip 18 includes an indicator layer 20 which is operable to change color in response to the change in the acidity of the vaginal fluid. In this regard, the indicator layer 20 is operable to change color when the pH of the vaginal fluid exceeds about 4.4. It is to be understood, however, that the level of acidity at which the indicator layer 20 changes color will depend upon the particular application for which the protective clothing article 10 is to be used. The indicator layer 20 is formed so that any coloring in the indicator layer 20 is not washed from the indicator layer 20 during use. While the indicator layer 20 may be part number 9542 available from Merck, Dormstadt, Germany other suitable materials may be used.

To attach the diagnostic strip 18 to the protective clothing article 10, the diagnostic strip 18 includes a two-sided adhesive strip 22. The adhesive strip 22 includes a handle or grip section 24 which does not have adhesive disposed thereon and therefore may be used to manipulate the adhesive strip 22 prior to being applied to the protective clothing article 10. By using the grip section 24, the diagnostic strip 18 connected on one side 26 of the adhesive strip 22 can be easily affixed to the protective clothing article 10 without touching the indicator layer 20. By avoiding direct contact with the indicator layer 20 during manipulation of the diagnostic strip 18, the possibility of contamination of the indicator layer 20 is reduced which might otherwise make another examination necessary. In addition, the use of a two-sided adhesive strip 22 also has the advantage that, on the one hand, the application of an adhesive to the protective clothing article 10 is avoided and, on the other hand, the quantity of adhesive is minimized and the adhesive is accurately positioned on the protective clothing article 10. Accordingly, contamination of the area region of the protective clothing article 10 to which the diagnostic strip 18 is to be applied, and in particular on the examination finger, by excess adhesive is avoided. Such contamination would make the protective clothing article 10 useless for the intended examination.

The method of the present invention will now be described with reference to FIG. 4 in which the area of the female pelvic depicted as a partial section is designated by 28. The protective clothing article 10 is initially slipped over the right hand with a diagnostic strip 18 placed on the index or examination finger 30. So as to attain a better wetting with the vaginal fluid, the index finger 30 is inserted into the vagina 32 with a slight rotation. The indicator layer 20 of the diagnostic strip 18 is inserted to a depth of up to 3 cm into the vagina 32 and is thereby colored in accordance with the existing pH value of the vaginal milieu. The index finger 30 with the protective clothing article 10 disposed thereon is then withdrawn from the vagina 32 and then the diagnostic strip 18 is compared to a scale to determine whether the pH exceeds approximately 4.4. If the pH level exceeds approximately 4.4, this is an indication that there may be a vaginal infection which should be treated to reduce the risk of having a premature birth. In the event that the pH level is below about 4.4, this is indicative of normal vaginal fluid and a reduced possibility that there is an immediate risk of a premature birth. In the event that the pH exceeds about 4.4, it is desirable to repeat the steps described above approximately one day later to protect against false positive indications.

Figure 5:
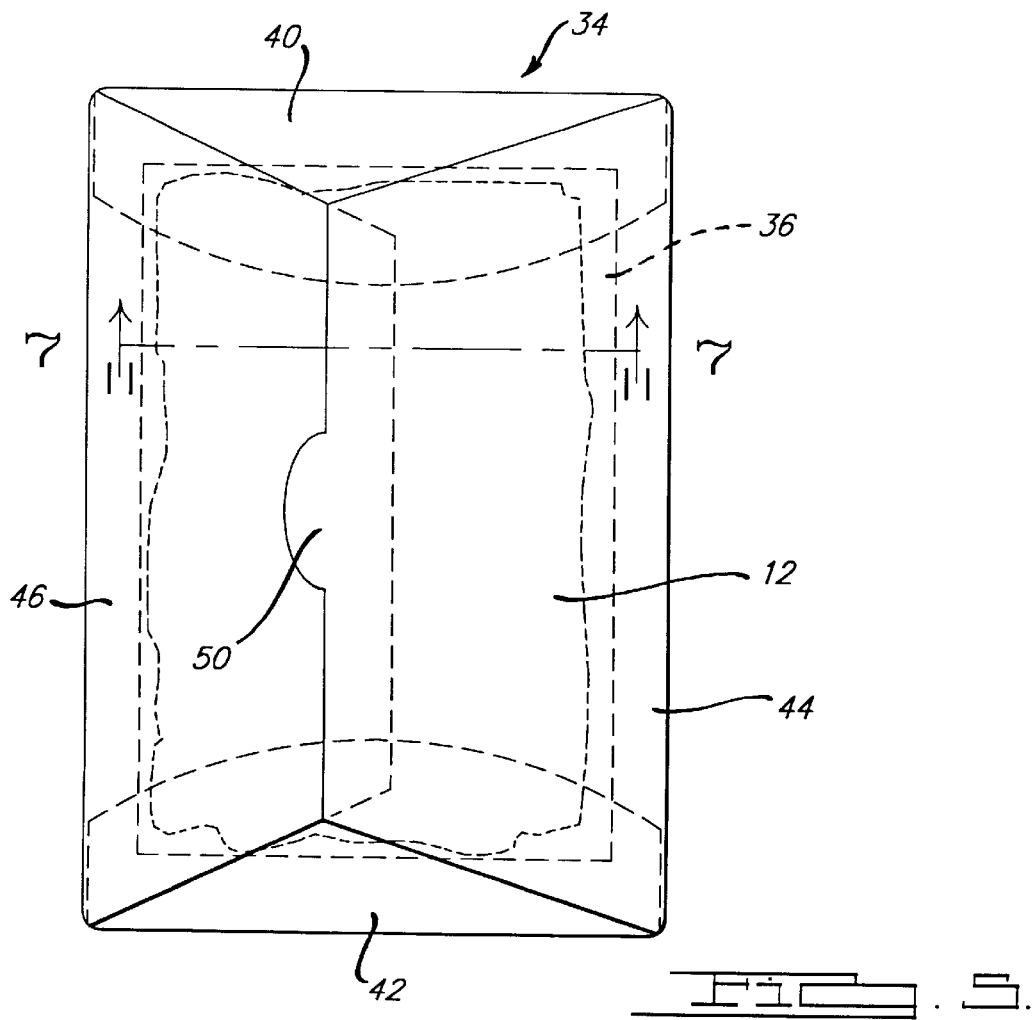
FIG. 5 is a top elevational view of the packaging used in connection with the apparatus for detecting an increased risk of premature birth in which the protective clothing article is in the form of a glove.

The packaging 34 used for storing the protective clothing article 10 in the form of a glove 12 will now be described with reference to FIGS. 5–7. The packaging 34 is preferably made of cardboard or a cardboard-like material and has printing which describes the contents of the packaging 34 as well as the manner of use of the protective clothing article 10. The packaging 34 has a bottom plate 36 in which a recess 38 is provided to receive the protective clothing article 10. On the side edges of the essentially rectangular bottom plate 36 are a plurality of foldable flaps 40–46 which are hinged with respect to the bottom plate 36. The flaps 40–46, which are located opposite one another, are folded pairwise such that the flaps 40–46 cover the bottom plate 36 with the flaps 40 and 42 pressed against the bottom plate 36 by the overlapping of the flaps 44 and 46. The free ends of the overlapping flaps 44 and 46 are temporarily secured to one another by an adhesive connection 48 provided on the edges of the flaps 44 and 46 as shown in FIG. 6. By pulling on the tear-open tab 50, the adhesive connection 48 can be overcome and the protective clothing article 10 can be removed from the packaging 34.

The position of a protective clothing article 10 within the packaging 34 which is designed for the glove 12 is shown in FIG. 7. The glove 12 is folded once transverse to the longitudinal extension of the fingers and lies in the recess 38 which is sealed by a thin protective film 52. The protective film 52 prevents an undesired influence of moisture on the contents of the packaging 34. A tear-open flap 54 placed on one side of the protective film 52 which permits relatively easy removal of the protective film 52 when the glove 12 is to be removed from the packaging 34. To open the packaging 34, the two overlapping flaps 44 and 46 are initially unfolded, wherein the adhesion connection 48 is mechanically loosened, and then the protective film 52 is removed by means of the tear-open flap 54.

Figure 8:
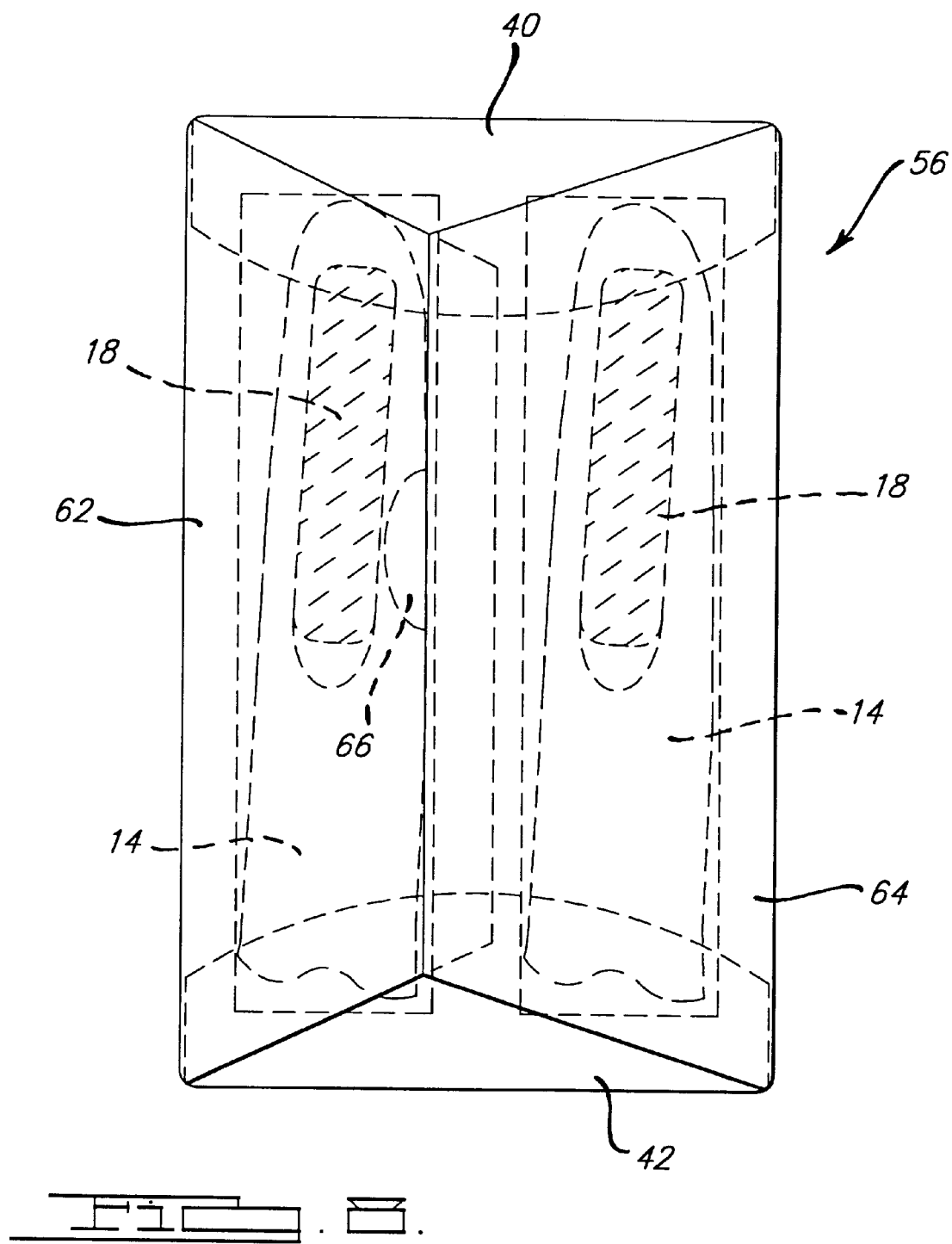
FIG. 8 is the packaging associated with the apparatus for detecting an increased risk of premature according to one preferred embodiment of the present invention in which the protective clothing article takes the form of a finger stall.

The packaging 56 used for storing the protective clothing article 10 in the form of a finger stall 14 is shown in FIGS. 8 and 9. The finger stalls 14 shown in FIG. 8 are placed in their extended form with the diagnostic strip 18 disposed upwards in recesses 58 provided in the bottom plate 60. The recesses 58 are hygienically closed by a protective film (not shown) which is similar to that described with respect to the packaging 34 shown in FIG. 7. The packaging 56 includes an overlapping flap 62 have a slit-shaped recess (not shown) and an overlapping flap 64 with a tab 66 on its free end which is able to be inserted into the recess so as to close the packaging 56.

Another preferred embodiment of the present invention will now be described with reference to FIG. 10 and FIG. 11, in which similar reference numerals will be used to identify similar elements. The apparatus according to this embodiment of the present invention includes a protective clothing article 10 which may take the form of either a glove 12 as shown in FIG. 10 or a finger stall 14 as shown in FIG. 11. The protective clothing article 10 includes a diagnostic strip 18 which is used for examining the vaginal milieu, particularly for determining the pH value of the vaginal fluid, and is secured to protective clothing article 10 by means of a double-sided adhesive strip 22.

The diagnostic strip 18 according to this embodiment of the present invention will now be described in a greater detail. The diagnostic strip 18 includes an indicator layer 20 and a covering layer 68. The indicator layer 20 is operable to change color in response to the pH of the endogenous fluid. In this regard, the indicator layer 20 is operable to change color when the pH of the vaginal fluid exceeds about 4.4. The covering layer 68 covers at least part of the indicator layer 20 so that the covered portions do not come into contact with the vaginal fluid during the examination of the vaginal milieu. In this regard, the covering layer 68 has a plurality of cutouts 70 which partially expose indicator layer 20 and permit a color change of the indicator layer 20 only in the region below the cutouts 70.

The covering layer 68 consists of a plastic film and is secured to the indicator layer 20 by adhesive. The covering layer 68 is preferably colored monochromatically and has a hue which corresponds with the hue of the indicator layer 20 if the vaginal fluid to which the indicator layer 20 is exposed has a pH value corresponding to a healthy vaginal milieu. Accordingly, the entire diagnostic strip 18 shows a single uniform, preferably a sunflower yellow color, if there is a healthy vaginal milieu. However, in the event of an unhealthy vaginal milieu, a direct comparison between the hue of the exposed areas of the indicator layer 28 and the hue of the immediately surrounding covering layer 68 permit even slight changes of color to be recognized by even medically unschooled persons, so that a more quantitatively precise gynecological examination can be initiated.

The covering layer 68 of the diagnostic strip 18 shown in FIG. 10 has cutouts 70 which are rectangularly shaped and become visible only in case of a change of color in the portions of the indicator layer 20 accessible to vaginal fluid.

Alternatively, the cutouts 70 in the covering layer 68 may be used to form a symbol which causes an additional psychological impact. For example, if hue covering layer 68 is shaped as the exclamation point 72 as shown in FIG. 11, this symbol becomes very visually conspicuous in case of a color transformation due to pathological changes of the vaginal milieu. Alternatively, the cutouts 70 may be shaped in the form of words or phrases such as "caution" or "warning" as shown in FIGS. 12 and 13 which may also provide an indication of pathological changes of the vaginal milieu.

As discussed above with respect to the embodiments shown in FIGS. 1–3, the diagnostic strip 18 shown in FIGS. 10–17 can be comfortably attached manually to the protective clothing article 10 by using an adhesive-free grip section 24 on the adhesive strip 22 without touching the indicator layer 20 or the substrate 74. The grip section 24 of the adhesive strip 22 permits easy handling of the diagnostic strip 18 when attaching the diagnostic strip 18 to the protective clothing article 10 immediately prior to the examination. It is equally advantageous that the indicator layer 20 of the diagnostic strip 18 need not be touched by the hand in order to position the diagnostic strip 18 to the desired point on the protective clothing article 10 so as to avoid contaminating the indicator layer 20 which might otherwise falsify the results of the examination and make a new examination necessary.

Another embodiment of the present invention is shown in FIGS. 15 and 16, in which similar reference numerals are used to identify similar elements. In this embodiment, the diagnostic strip 18 includes cutouts 70 forming an exclamation mark as well as a color scale 76 which is arranged on the outside of the diagnostic strip 18 and extends parallel to its longitudinal axis. The color scale 76 has a number of color gradations 78 for analytical purposes with which the hue of the uncovered surface sections of the indicator layer 20 can be easily compared.

The diagnostic strips 18 according to any of the embodiments described herein may be stored in a manner shown in FIG. 17 using a tear-off roll 80 on which are located a number of the diagnostic strips 18. The individual diagnostic strips 18 are arranged detachably in sequence on a carrier strip 82 and can be removed from the roll 80 as needed. In order to ease the separation of the diagnostic strips 18, the carrier strip 18 has a planned tearing point 84 between each two adjacent diagnostic strips 18. After removing the carrier strip 82 from the double-sided adhesive strip 22, the corresponding diagnostic strip 18 can be applied to the protective clothing article 10.

Another preferred embodiment of the present invention is shown in FIGS. 18 and 19 in which similar reference numerals are used to indicate similar elements. The apparatus according to these embodiments of the present invention include a diagnostic strip 18 which is located distally of the region 86 of the protective clothing article 10 which corresponds to the first finger joint 90 of the hand. The diagnostic strip 28 is relatively small and has a distal edge 88 which is generally circular to facilitate insertion into the vagina 32. By making the diagnostic strip 18 relatively small and located distally of the first finger joint 90, there is less of an opportunity for a color variation to occur within the diagnostic strip 18 and therefore less of a chance that the results will be incorrectly interpreted.

The protective clothing article 10 may also have a scale 92 which is disposed in an area which is not used during examination (e.g., near the palm of the glove 12). By locating scale 92 on the protective clothing article 10, a relatively easy comparison can be made between the color of the diagnostic strip 18 and the scale 92.

Figure 20:
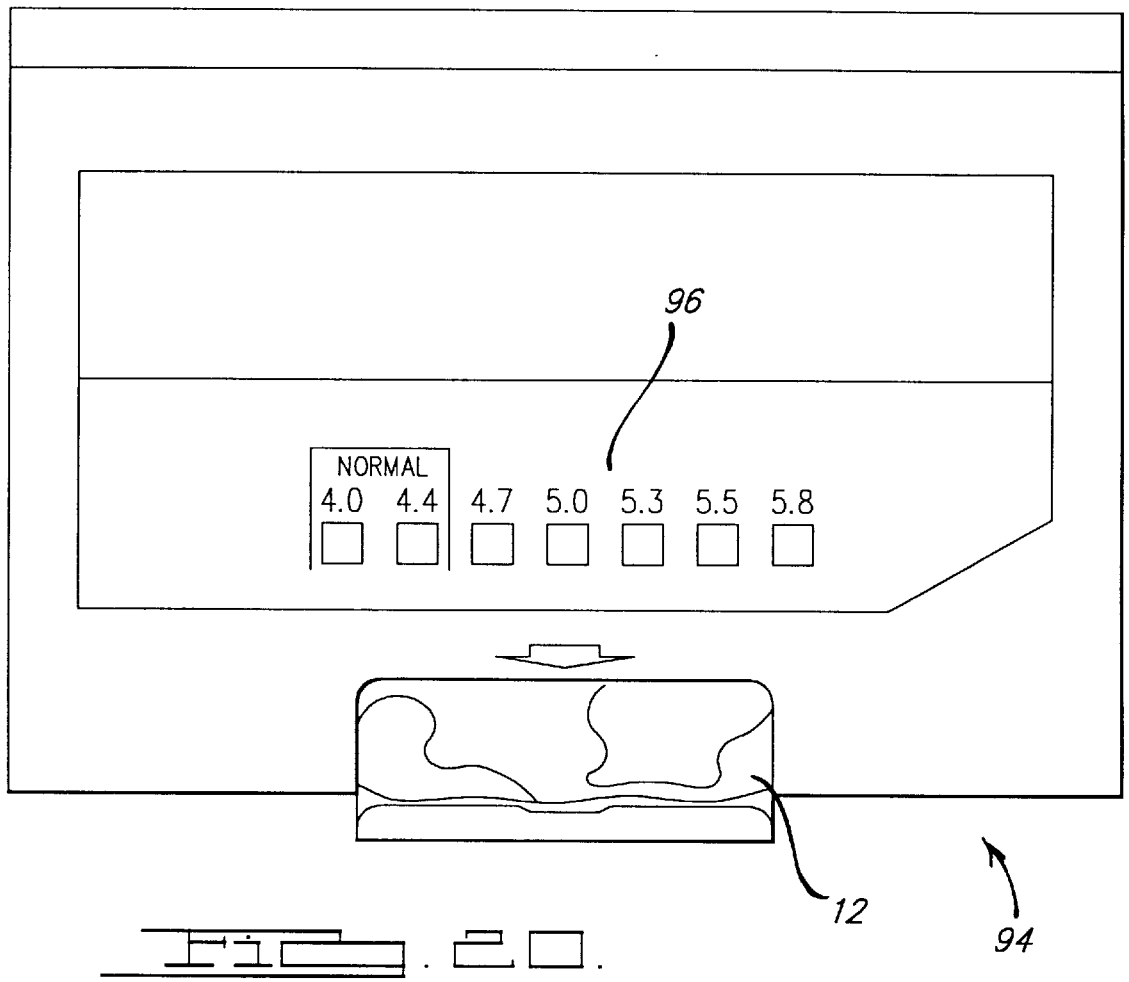
FIG. 20 is an elevational view of the packaging used to store the apparatus for detecting the increased risk of premature birth according to the preferred embodiment of the present invention.

The protective clothing article 10 may also be stored in another packaging 94 which is shown in FIG. 20. In this regard, the packaging 94 is used to store a plurality of protective clothing articles 10 which may be sequentially used. The packaging 94 includes a pH scale 96 which may be used to compare the color of the diagnostic strip 18 of the protective clothing articles 10 after examination. In this regard, the packaging 94 includes a visual indication of which color is within the range of a healthy vaginal milieu and which color does not corresponding to a healthy vaginal milieu.

While the above detailed description describes the preferred embodiment of the present invention, it will be understood that the present invention is susceptible to modification, variation and alteration without deviating from the scope and fair meaning of the subjoined claims.

What is claimed is:

1. An apparatus for use in measuring the properties of endogenous fluids during a medical examination, said apparatus comprising:

a protective clothing article operable to be used during the medical examination and including a glove having an index finger section;

a diagnostic strip which is operable to measure the pH of endogenous fluid during the medical examination; and a two-sided adhesive strip operable to secure said diagnostic strip to said index finger section of said glove.

2. The apparatus for use in measuring the properties of endogenous fluids during a medical examination according to claim 1, wherein said diagnostic strip includes an indicator layer which is operable to change color in response to change in the acidity of the endogenous fluids.

3. An apparatus for use in measuring the properties of endogenous fluids during a medical examination, said apparatus comprising: a protective clothing article apparatus to be used during the medical examination, said protective clothing article including a finger stall;

a diagnostic strip which is operable to measure the pH of endogenous fluid during the medical examination; and a two-sided adhesive strip operable to affix said diagnostic strip to said finger stall.

4. The apparatus for use in measuring the properties of endogenous fluids during a medical examination according to claim 1, or 3, wherein said protective clothing article is made of polyethylene.

5. The apparatus for use in measuring the properties of endogenous fluids during a medical examination according to claim 1, or 3, wherein said adhesive strip includes an adhesive-free grip section being operable to facilitate attachment of said diagnostic strip to said protective clothing article.

6. The apparatus of claim 1 or 3, wherein said diagnostic strip includes:

(a) an indicator layer, (b) a covering layer which partially covers said indicator layer, said covering layer defining covered portions and uncovered portions on said indicator layer, said uncovered portions being exposed to endogenous fluids during the medical examination and said covered portion not being exposed to endogenous fluids during the medical examination, said covering layer being of a color substantially corresponding to the color of said indicator layer prior to the medical examination as well as after the medical examination when the endogenous fluid is within specified range of acidity.

7. The apparatus for use in measuring the properties of an endogenous fluid as set forth in claim 6, wherein said covering layer includes cutouts through which the endogenous fluid comes into contact with said indicator layer.

8. The apparatus for use in measuring the properties of an endogenous fluid as set forth in claim 7, wherein said cutouts have a shape selected from the group consisting of circular or square.

9. The apparatus for use in measuring the properties of an endogenous fluid as set forth in claim 7, wherein said cutouts form a symbol which can be recognized as a warning indication.

10. The apparatus for use in measuring the properties of an endogenous fluid as set forth in claim 9, wherein said symbol forms a caution symbol.

11. The apparatus for use in measuring the properties of an endogenous fluid as set forth in claim 9, wherein said symbol forms an exclamation mark.

12. The apparatus for use in measuring the properties of an endogenous fluid as set forth in claim 9, wherein said symbol forms a conventional warning sign or a conventional written warning.

13. The apparatus for use in measuring the properties of an endogenous fluid as set forth in claim 7, wherein said covering layer is formed from a transparent film.

14. The apparatus for use in measuring the properties of an endogenous fluid as set forth in claim 13, wherein said covering layer is held in place on said indicator layer by adhesion.

15. The apparatus for use in measuring the properties of an endogenous fluid as set forth in claim 14, wherein said covering layer consists of plastic and is colored monochromatically.

16. The apparatus for use in measuring the properties of an endogenous fluid as set forth in claim 15, wherein said apparatus is operable to determine the pH of vaginal fluid, the coloration of said covering layer corresponding to the hue which said indicator layer becomes if the vaginal fluid has a pH value corresponding to a healthy vaginal milieu.

17. The apparatus for use in measuring the properties of an endogenous fluid as set forth in claim 16, wherein said covering layer has a sunflower-yellow coloration.

18. The apparatus for use in measuring the properties of an endogenous fluid as set forth in claim 6, wherein said covering layer further includes a color scale having essentially all the colors which said indicator layer acquires during the examination of vaginal fluid.

19. The apparatus for use in measuring the properties of an endogenous fluid as set forth in claim 18, wherein said color scale includes hues in gradations from sunflower yellow to ocher brown.

20. The apparatus for use in measuring the properties of an endogenous fluid as set forth in claim 18, wherein said color scale extends in the direction of the longitudinal axis of the diagnostic strip.

21. The apparatus for use in measuring the properties of an endogenous fluid as set forth in claim 6, characterized by a substrate imprinted with said indicator layer.

22. The apparatus for use in measuring the properties of an endogenous fluid as set forth in claim 6, further comprising a double-sided adhesive strip joined on one side to said indicator layer and on the other side to said protective clothing article.

23. The apparatus for use in measuring the properties of an endogenous fluid as set forth in claim 22, wherein said adhesive strip includes an adhesive-free grip section located on one end of said adhesive strip operable to be used for facilitating attachment of said diagnostic strip to said protective clothing article.

24. The apparatus for use in measuring the properties of an endogenous fluid as set forth in claim 6, further comprising a plurality of diagnostic strips which are sequentially disposed on a carrier strip that can be wound up into a tear-off roll.

25. The apparatus for use in measuring the properties of endogenous fluid as set forth in claim 24, wherein the longitudinal axis of the diagnostic strip extends parallel to the longitudinal axis of the carrier strip.

26. An apparatus for use in measuring the properties of endogenous fluids during a medical examination, said apparatus comprising:
   a protective clothing article operable to be used during the medical examination;
   a diagnostic strip which is operable to measure the pH of endogenous fluid during the medical examination; and
   a two-sided adhesive strip operable to secure said diagnostic strip to a portion of said protective clothing article;
   wherein the apparatus is operable to determine the pH of vaginal fluid, the coloration of said diagnostic strip corresponding to the hue which said indicator layer becomes if the vaginal fluid has a pH value corresponding to a healthy vaginal milieu.

27. The apparatus for use in measuring the properties of endogenous fluids during a medical examination according to claim 26, wherein said diagnostic strip includes an indicator layer which is operable to change color in response to change in the acidity of the endogenous fluids.

28. The apparatus for use in measuring the properties of endogenous fluids during a medical examination according to claim 26, wherein said protective clothing article comprises a finger stall.

29. The apparatus for use in measuring the properties of endogenous fluids during a medical examination according to claim 26, wherein said protective clothing article is made of polyethylene.

30. The apparatus for use in measuring the properties of endogenous fluids during a medical examination according to claim 26, wherein said adhesive strip includes an adhesive-free grip section being operable to facilitate attachment of said diagnostic strip to said protective clothing article.

* * * * *

UNITED STATES PATENT AND TRADEMARK OFFICE
CERTIFICATE OF CORRECTION

PATENT NO.   : 6,123,676
DATED        : September 26, 2000
INVENTOR(S)  : Emmanuel Anapliotis It is certified that error appears in the above-identified patent and that said Letters Patent is hereby corrected as shown below:

Column 3,
Line 26, after "premature" insert -- birth --.

Column 6,
Line 18, delete "have" and substitute -- having -- therefor.

Column 7,
Line 45, "carrier strip 18" should be -- carrier strip 82 --.
Line 57, "diagnostic strip 28" should be -- diagnostic strip 18 --.

Column 8,
Line 12, delete "corresponding" and substitute -- correspond -- therefor.

Signed and Sealed this

Twenty-sixth Day of March, 2002

*Attest:*

JAMES E. ROGAN
*Attesting Officer*       *Director of the United States Patent and Trademark Office*